United States Patent
Somaya

(10) Patent No.: US 9,138,198 B2
(45) Date of Patent: Sep. 22, 2015

(54) ELECTRIC ARC DETECTION FOR X-RAY GENERATORS

(71) Applicant: General Electric Company, Schenectady, NY (US)

(72) Inventor: Sinivassane Somaya, Longjumeau (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 129 days.

(21) Appl. No.: 13/953,927

(22) Filed: Jul. 30, 2013

(65) Prior Publication Data

US 2014/0029723 A1    Jan. 30, 2014

(30) Foreign Application Priority Data

Jul. 30, 2012 (FR) ...................... 12 57368

(51) Int. Cl.
*G01D 18/00* (2006.01)
*A61B 6/00* (2006.01)
*H05G 1/26* (2006.01)

(52) U.S. Cl.
CPC . *A61B 6/586* (2013.01); *H05G 1/26* (2013.01)

(58) Field of Classification Search
CPC ............. H05G 1/54; H05G 1/34; H01J 35/02; H01J 35/26; H01J 35/16; A61B 6/586
USPC .................. 378/117, 118, 121, 207
See application file for complete search history.

(56) References Cited

U.S. PATENT DOCUMENTS

| 6,757,356 B2 * | 6/2004 | Yagi ............................... 378/118 |
| 7,110,499 B2 | 9/2006 | Beyerlein et al. |
| 2005/0199058 A1 * | 9/2005 | Danz et al. ........................ 73/455 |

FOREIGN PATENT DOCUMENTS

| DE | 4226234 | 2/1994 |
| JP | 61-153932 | 7/1986 |
| JP | 02-207496 | 8/1990 |
| JP | 05-002047 | 1/1993 |
| JP | 2002-191105 | 7/2002 |
| JP | 2005-135785 | 5/2005 |
| JP | 2010-110181 | 5/2010 |

OTHER PUBLICATIONS

French Search Report from corresponding French Application No. 1257368, Dated Mar. 25, 2013.

* cited by examiner

*Primary Examiner* — Courtney Thomas
(74) *Attorney, Agent, or Firm* — GE Global Patent Operation; Marc A. Vivenzio

(57) ABSTRACT

A method for detecting electric arcs on an X-ray generator, the method comprising recording mechanical vibrations of an environment of the X-ray generator, the X-ray generator, or elements of the X-ray generator, using at least one sensor configured to record vibrations to record vibrations, and processing signals recorded by the at least one sensor to identify peaks corresponding to the formation of the electric arcs.

16 Claims, 2 Drawing Sheets

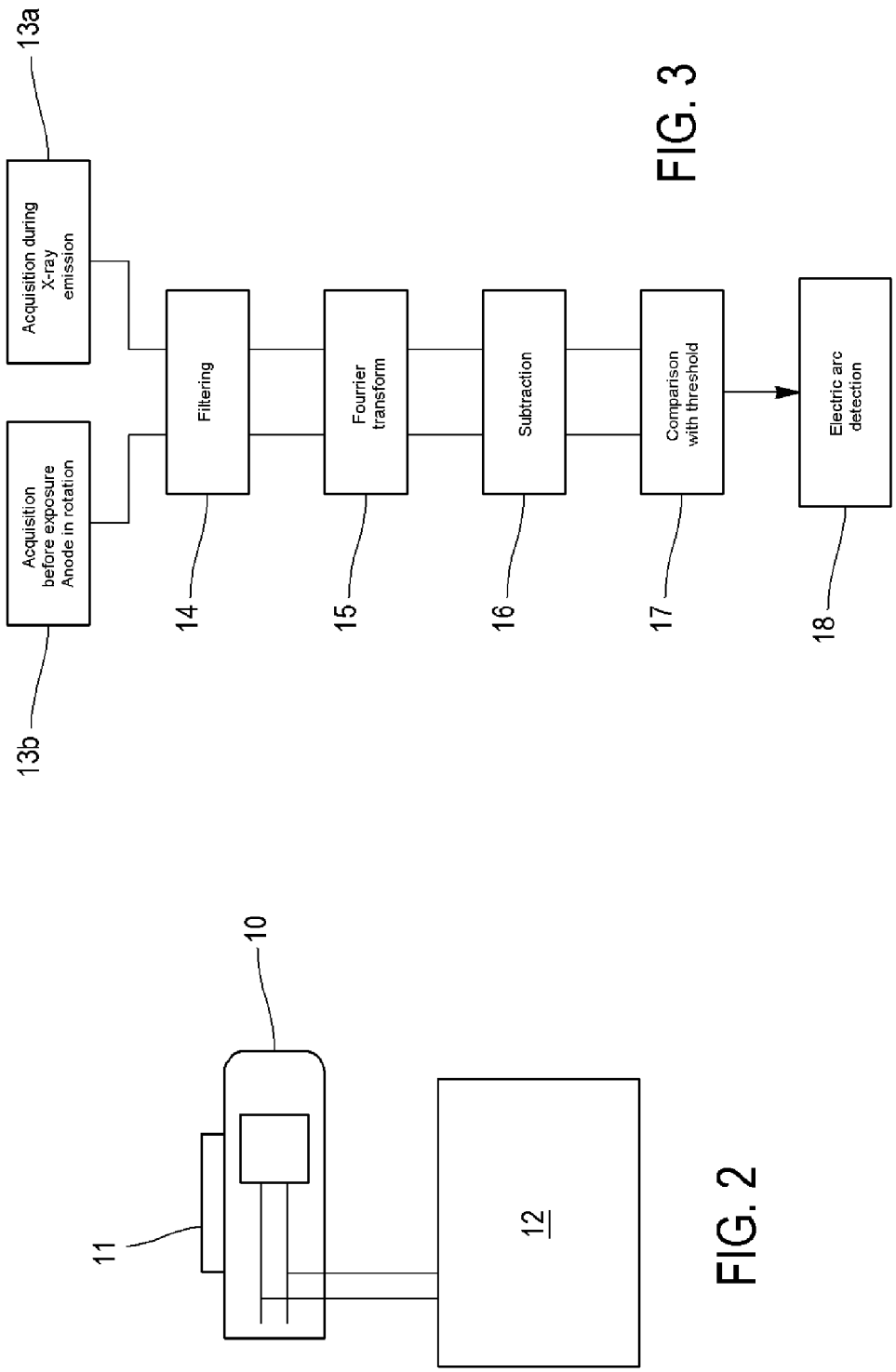

ELECTRIC ARC DETECTION FOR X-RAY GENERATORS

BACKGROUND OF THE INVENTION

Embodiments of the present invention relate to X-ray generators used in medical imaging and, in particular, to X-ray generators used in functional imaging, mammography, fluoroscopic imaging, etc.

Conventionally, said generators comprise an X-ray tube and a high voltage generator which delivers the high voltage and the current to said tube needed for the functioning thereof.

This high voltage generator and this tube integrate a certain number of electrically insulating dielectric components (oil of the lamp of the X-ray tube, transformer oil, insulating plastic for connections between the generator and tube, insulating material of the generator's electronic components, etc. . . . ), which, on account of the presence of impurities or fatigue of their dielectric characteristics, can be the site of high voltage discharges and the generation of electric current arcs.

In some applications in particular, these high voltage discharges can be particularly critical having a substantial impact on imaging results. For example, in fluoroscopy, they may necessitate the interruption of an image taking session even though a contrast agent has already been injected into a patient.

In addition, these electric arcs may also cause major degradation of the equipment.

In particular, it is desirable to be able to act very rapidly to change faulty parts when electric arcs start to occur, so as to prevent the repeated formation of electric arcs at one part from further degrading the entire equipment and from extending to all the components thereof.

There is therefore a need for the easy, efficient detection of the formation of electric arcs on X-ray emitting devices used in medical imaging.

In addition, it is desirable to be able to reduce the on-site servicing time of the technicians in charge of changing the parts of equipment on which electric arcs have started to be generated. However, at the present time technicians have to carry out repairs on equipment without knowing which part is faulty and without knowing whether the fault lies with the X-ray tube or the generator. Much time is therefore spent in searching for the site of the fault and it may even happen that technicians are unable to detect precisely which part has to be changed.

There is also a need for detection which allows the facilitated locating of faulty parts on which electric arcs are triggered.

BRIEF DESCRIPTION OF THE INVENTION

Embodiments of the present invention overcome all or part of these disadvantages of the prior art.

According to an embodiment, there is provided a method for detecting electric arcs on X-ray generators according to which mechanical vibrations in the generator environment are recorded, or on the generator or on elements of said generator, using at least one sensor capable of detecting such vibrations, and the signals recorded by the sensor or sensors are processed so as to evidence on said signals the peaks corresponding to the formation of electric arcs.

According to an embodiment, the sensor is a microphone, an accelerometer or an ultrasound detector.

According to an embodiment, there is provided a device for detecting electric arcs on X-ray generators, the device comprising a sensor capable of detecting mechanical vibrations in the generator environment, or on the generator or on elements of said generator.

According to an embodiment an assembly comprising a said detection device and an X-ray generator and a medical imaging system comprising said device.

According to an embodiment, there is provided a device for detecting electric arcs on an X-ray generator. The device comprises at least one sensor configured to record mechanical vibrations of an environment of the X-ray generator, the X-ray generator, or elements of the X-ray generator.

According to an embodiment, there is provided a medical imaging system. The medical imaging system comprises an X-ray generator mounted on a support, an array of detectors facing the X-ray generator, and a device configured to detect electric arcs, the device comprising at least one sensor configured to record mechanical vibrations of an environment of the X-ray generator, the X-ray generator, or elements of the X-ray generator.

BRIEF DESCRIPTION OF THE DRAWINGS

Other characteristics and advantages of the invention will become further apparent from the following description which is solely illustrative and non-limiting and is to be read in connection with the appended Figures in which:

FIG. 2 schematically illustrates a detection device conforming to an embodiment of the present invention; and FIG. 3 illustrates a method for detecting electric arcs on an X-ray generator according to an embodiment of the present invention.

DETAILED DESCRIPTION

Figure 1:
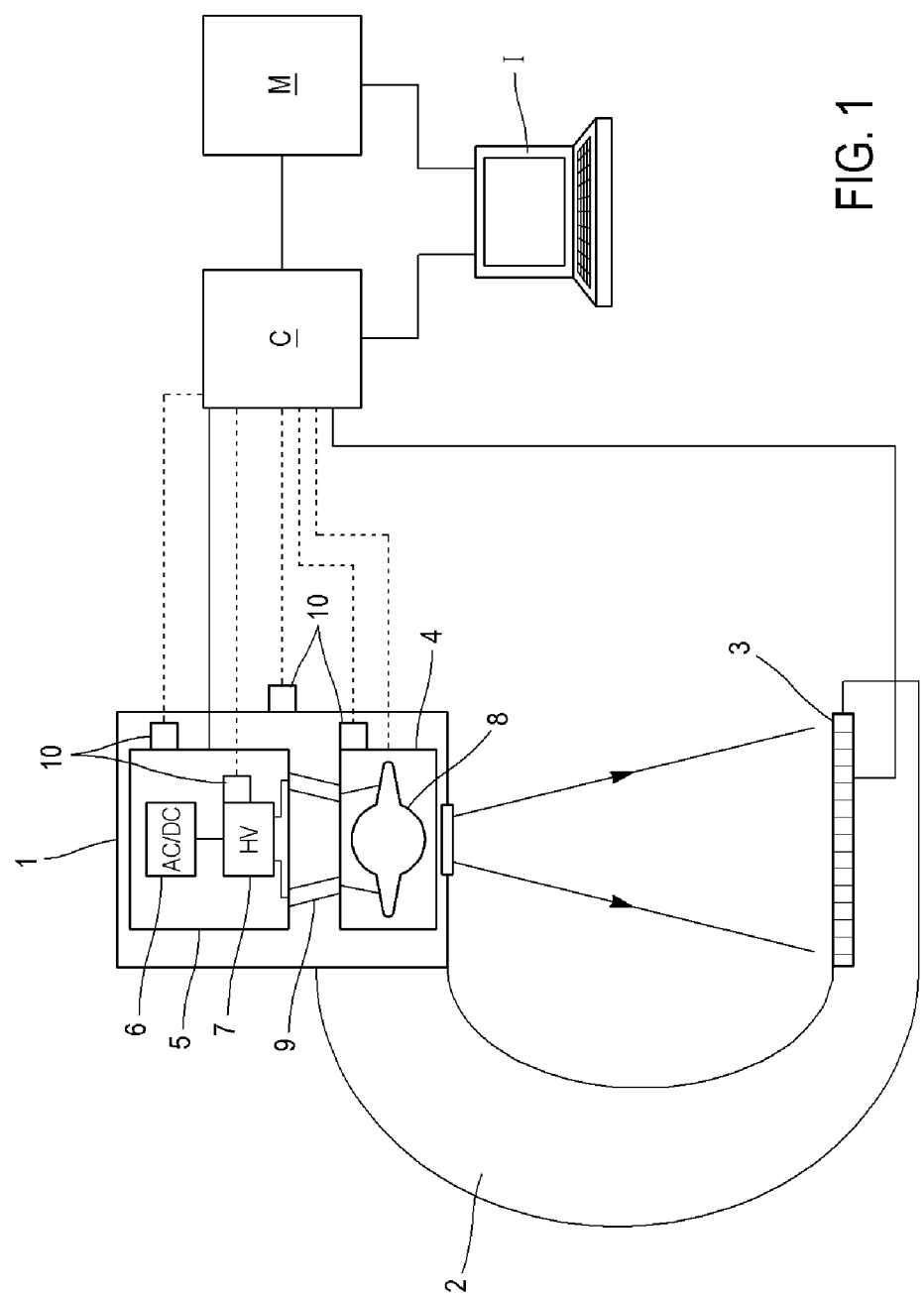
FIG. 1 schematically illustrates a medical imaging system comprising a device for detecting electric arcs having several vibration sensors according to an embodiment of the present invention.

According to an embodiment of the present invention, there is provided an imaging device.

FIG. 1 schematically illustrates an imaging device which here is of C-arm type.

It comprises an X-ray generator 1 mounted on a C-arm 2 forming a support and also carrying a sensor 3 arranged on said C-arm 2 and facing the X-ray generator 1.

As is conventional, this sensor 3 is in the form of an array of detectors associated with analogue/digital converters and is connected to a computer C which carries out processing on the acquired images and optionally controls the X-ray generator 1.

This computer C is also connected to a storage device M which stores in memory the acquired and processed images, and to an interface I allowing the controlling of the imaging device assembly, the visualization of acquired images and control over the processing thereof.

The generator 1 comprises an X-ray tube 4 and a high voltage generator 5 in the form of a casing notably integrating several stages of electric energy conversion 6 (AC/DC, DC/DC, DC/AC rectifiers) and a high voltage transformer 7. This high voltage generator 5 also integrates an oil circuit intended for cooling and electric insulation, and different insulating components. Its transformer is connected to the cathode and anode of the X-ray lamp 8 of the tube 4 via connections which themselves are insulated.

According to an embodiment of the present invention, there is provided a detection device.

As illustrated in FIG. 1, one or more mechanical sensors 10 can be integrated in or added onto the high voltage generator 5, or onto the X-ray tube 4 or onto the generator 1, or onto the support which here is formed by the C-arm 2.

These may in particular be fully independent relative to the imaging device and can be fixed for example by magnetization onto the casing of the X-ray generator 1, or onto the casing of the high voltage generator 5 or even on the insulating body of the X-ray tube 4.

In an embodiment, one or more mechanical sensors 10 can be fully integrated in the X-ray generator 1, or in the casing of the high voltage generator 5 or in the X-ray tube 4, specific housings possibly being provided for this purpose on the casing or body of one and/or the other for the receiving thereof.

Different types of mechanical sensors can be used for the sensors 10, to record mechanical vibrations of the generator 1 and of its environment. In an embodiment, the sensors 10 may be microphones or accelerometers. They may also be ultrasound sensors.

The mechanical sensor 10 illustrated in FIG. 2 is a magnetized accelerometer (magnetization 11) which is associated with a detection circuit 12, independent of the computer C, allowing the voltage conversion of the charges of the accelerometer and the amplification thereof, and optionally filtering or detecting operations on the recorded signals, these operations possibly being conducted by said circuit 12, or by the computer C or a by separate processor. The output signals from this circuit 12 for this purpose can be sent to the computer C for example, or directly to the interface I. The output signals can also be sent to a separate processor and interface.

The accelerometer 10 here is a piezoelectric accelerometer, other types of accelerometers possibly being used however: resistive, capacitive, servo-controlled, etc.

Accelerometers of piezoelectric type are able to withstand high temperatures (up to 700° C.) and allow measurements over a wide scale (from $10^{-5}$ to $10^5$ g). They are sensitive to variations of small amplitude, and are little voluminous. They have very wide frequency response (from 0.5 to 50 kHz).

The processing circuit 12 associated with the sensor 10, the computer C or a separate processor onto which the output signals from the processing circuit 12 are sent, perform processing on the recorded signals allowing the discrimination of signal peaks due to electric arcs among the total noise of the environment of imaging devices.

It is known that imaging devices, scanners in particular, can be relatively noisy and when in use can generate much mechanical jolting which must be distinguished from signals due to electric arcs.

For this purpose, as illustrated in FIG. 3, the signals obtained are subjected within the processing chain to at least one band-pass or high frequency filtering operation 14. Different types of filtering can evidently be used.

Also, to facilitate processing, they are switched from the time domain to the frequency domain using processing of Fourier transform type 15. Therefore all or part of the processing is performed in the frequency domain.

In addition, to eliminate background noise due to rotation of the anode of the lamp of the tube 4, or in the case for example when the imaging device is a scanner the background noise due to rotation of the generator 1 on the axis of the scanner, processing entails the subtracting 16 of the signals acquired by the sensor 10 when in operation and in particular during an exposure time and hence when the generator 1 is powered up 13a, from the signals acquired when the anode, the lamp and optionally the scanner are in rotation but the generator 1 is not powered up 13b.

The filtered, subtracted signals thus obtained in the frequency domain are then compared with a detection threshold whose level is previously determined in relation to the desired sensitivity for the detection device 17.

The peaks above the chosen threshold are detected electric arcs. When these peaks are detected 18, the interface I or the interface with which the processing card 12 or associated processor is connected, generates an alert signal in the form of a sound signal for example or the display of an alert message.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for detecting electric arcs on an X-ray generator, the method comprising:
   recording mechanical vibrations of an environment of the X-ray generator, the X-ray generator, or elements of the X-ray generator;
   using at least one sensor configured to record vibrations to record vibrations; and
   processing signals recorded by the at least one sensor to identify peaks corresponding to the formation of the electric arcs.

2. The method according to claim 1, wherein processing signals recorded by the at least one sensor comprises using at least a band-pass or a high frequency filtering operation.

3. The method according to claim 1, wherein processing signals recorded by the at least one sensor comprises applying processing of at least one Fourier transform on the signals, wherein at least part of processing signals recorded by the at least one sensor is conducted in the frequency domain.

4. The method according to claim 1, wherein processing signals recorded by the at least one sensor comprises comparing a first set of signals corresponding to vibrations recorded during a first phase when the X-ray generator is powered up and is emitting, and a second set of signals corresponding to vibrations recorded during a second phase when the X-ray generator is not emitting, but the X-ray generator, the elements of the X-ray generator, or the environment of the X-ray generator are in movement.

5. The method according to claim 4, further comprising:
   subtracting the second set of signals corresponding to the vibrations recorded during the second phase from the first set of signals corresponding to the vibrations recorded during the first phase to obtain a third set of signals; and
   comparing the third set of signals with a detection threshold.

6. A device for detecting electric arcs on an X-ray generator, the device comprising:
   at least one sensor configured to record mechanical vibrations of an environment of the X-ray generator, the X-ray generator, or elements of the X-ray generator; and a circuit configured to receive at least one signal from the at least one sensor and process the at least one signal to identify peaks corresponding to the formation of the electric arcs.

7. The device according to claim 6, wherein the at least one sensor is a microphone, an accelerometer, or an ultrasound detector.

8. The device according to claim 7, wherein the at least one sensor is a piezoelectric accelerometer.

9. The device according to claim 6, wherein the at least one sensor is magnetized.

10. The device according to claim 6, wherein the circuit is further configured to compare a first set of signals corresponding to vibrations recorded during a first phase when the X-ray generator is powered up and is emitting, and a second set of signals corresponding to vibrations recorded during a second phase when the X-ray generator is not emitting, but the X-ray generator, the elements of the X-ray generator, or the environment of the X-ray generator are in movement.

11. The device according to claim 10, wherein the circuit is further configured to subtract the second set of signals corresponding to the vibrations recorded during the second phase from the first set of signals corresponding to the vibrations recorded during the first phase to obtain a third set of signals, and to compare the third set of signals with a detection threshold.

12. An assembly comprising an X-ray generator and the device according to claim 6, wherein the assembly is arranged in the environment of the X-ray generator, on the X-ray generator, or on one of the elements of the X-ray generator.

13. The assembly according to claim 12, wherein a casing of the X-ray generator, a casing of a high voltage generator of the X-ray generator, and/or a body of an X-ray tube of the X-ray generator are adapted with a housing to receive the at least one sensor.

14. A medical imaging system, comprising:
an X-ray generator mounted on a support;
an array of detectors facing the X-ray generator; and
a device configured to detect electric arcs, the device comprising at least one sensor configured to record mechanical vibrations of an environment of the X-ray generator, the X-ray generator, or elements of the X-ray generator, and a circuit configured to receive at least one signal from the at least one sensor and process the at least one signal to identify peaks corresponding to the formation of the electric arcs.

15. The medical imaging system according to claim 14, wherein the circuit is further configured to compare a first set of signals corresponding to vibrations recorded during a first phase when the X-ray generator is powered up and is emitting, and a second set of signals corresponding to vibrations recorded during a second phase when the X-ray generator is not emitting, but the X-ray generator, the elements of the X-ray generator, or the environment of the X-ray generator are in movement.

16. The medical imaging system according to claim 15, wherein the circuit is further configured to subtract the second set of signals corresponding to the vibrations recorded during the second phase from the first set of signals corresponding to the vibrations recorded during the first phase to obtain a third set of signals, and to compare the third set of signals with a detection threshold.

* * * * *